United States Patent
Hyung et al.

(10) Patent No.: US 10,022,288 B2
(45) Date of Patent: Jul. 17, 2018

(54) TORQUE SETTING METHOD AND APPARATUS

(71) Applicant: Samsung Electronics Co., Ltd., Suwon-si, Gyeonggi-do (KR)

(72) Inventors: Seungyong Hyung, Yongin-si (KR); Youngjin Park, Seoul (KR); Youngbo Shim, Seoul (KR); Sunghwan Ahn, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 210 days.

(21) Appl. No.: 14/971,146

(22) Filed: Dec. 16, 2015

(65) Prior Publication Data

US 2017/0035640 A1 Feb. 9, 2017

(30) Foreign Application Priority Data

Aug. 4, 2015 (KR) .................. 10-2015-0109978

(51) Int. Cl.
*A61H 3/00* (2006.01)
*A61H 1/02* (2006.01)
(Continued)

(52) U.S. Cl.
CPC .............. *A61H 3/00* (2013.01); *A61B 5/1071* (2013.01); *A61B 5/112* (2013.01); *A61F 5/0102* (2013.01); *A61H 1/0244* (2013.01); *A61B 5/0488* (2013.01); *A61F 2005/0155* (2013.01); *A61H 2201/0165* (2013.01); *A61H 2201/1215* (2013.01); *A61H 2201/164* (2013.01); *A61H 2201/165* (2013.01);
(Continued)

(58) Field of Classification Search
CPC ....... A61H 3/00; A61H 1/0244; A61F 5/0102; A61B 5/1071; A61B 5/112; B25J 9/1653; B25J 9/1694
USPC ........................................ 700/253, 245, 261
See application file for complete search history.

(56) References Cited

U.S. PATENT DOCUMENTS 8,417,382 B2 * 4/2013 Yoshiike .............. B62D 57/032
700/245
8,473,102 B2 * 6/2013 Andoh ................. B62D 57/032
700/245

(Continued)

FOREIGN PATENT DOCUMENTS

JP        4669847 B2      4/2011
JP     2012-066375 A      4/2012

(Continued)

OTHER PUBLICATIONS

S. Lee, Y. Saki, "Power Assist Control for Walking Aid with HAL-3 Based on EMG and Impedance Adjustment around Knee Joint", Intelligent Robots and Systems, 2002. IEEE/RSJ International Conference, vol. 2, pp. 1499-1504.

*Primary Examiner* — Patrick H Mackey
(74) *Attorney, Agent, or Firm* — Harness, Dickey & Pierce, P.L.C.

(57) ABSTRACT

Provided is a method and apparatus for setting a torque of a walking assistance apparatus. A rotation angle and a rotation angular velocity of the walking assistance apparatus may be measured to set the torque. An amount of torque to be set may be calculated based on the rotation angle and the rotation angular velocity of the walking assistance apparatus.

20 Claims, 12 Drawing Sheets

(51) Int. Cl.
*A61B 5/11* (2006.01)
*A61F 5/01* (2006.01)
*A61B 5/107* (2006.01)
*A61B 5/0488* (2006.01)

(52) U.S. Cl.
CPC ........... *A61H 2201/5005* (2013.01); *A61H 2201/5007* (2013.01); *A61H 2201/5012* (2013.01); *A61H 2201/5048* (2013.01); *A61H 2201/5058* (2013.01); *A61H 2201/5061* (2013.01); *A61H 2201/5069* (2013.01); *A61H 2201/5071* (2013.01); *A61H 2201/5079* (2013.01); *A61H 2201/5084* (2013.01); *A61H 2201/5097* (2013.01); *A61H 2230/605* (2013.01)

(56) References Cited

U.S. PATENT DOCUMENTS

| | | | |
|---|---|---|---|
| 8,801,641 B2 | 8/2014 | Kazerooni et al. | |
| 9,221,177 B2* | 12/2015 | Herr | B25J 9/1694 |
| 2011/0301756 A1* | 12/2011 | Yoshiike | B62D 57/032 |
| | | | 700/253 |
| 2013/0150980 A1* | 6/2013 | Swift | A61F 2/68 |
| | | | 623/24 |
| 2014/0100494 A1 | 4/2014 | Sarkodie-Gyan et al. | |
| 2014/0121782 A1 | 5/2014 | Herr et al. | |
| 2015/0051710 A1 | 2/2015 | Herr et al. | |
| 2015/0127018 A1* | 5/2015 | Lim | A61H 3/00 |
| | | | 606/130 |
| 2016/0229055 A1* | 8/2016 | Kim | B25J 9/1633 |

FOREIGN PATENT DOCUMENTS

| | | | |
|---|---|---|---|
| JP | 2013-066669 A | | 4/2013 |
| KR | 20140118219 A | * | 10/2014 |
| KR | 2015062285 A | * | 6/2015 |
| WO | WO-2013-094747 A1 | | 6/2013 |

\* cited by examiner

TORQUE SETTING METHOD AND APPARATUS

CROSS-REFERENCE TO RELATED APPLICATION

This application claims under 35 U.S.C. § 119 to Korean Patent Application No. 10-2015-0109978, filed on Aug. 4, 2015, in the Korean Intellectual Property Office, the entire contents of which are incorporated herein by reference in its entirety.

BACKGROUND

1. Field

At least one example embodiment relates to a torque setting method and/or apparatus. For example, at least some example embodiments relate to a torque setting method and/or apparatus based on a rotation angle and a rotation angular velocity of a walking assistance apparatus.

2. Description of the Related Art

With developments in robot technology, research on improving a human ability through a mechanical assistance is being actively conducted. Among technologies for improving a human ability, research on enhancing a muscle strength is garnering attention. People performing tasks that require muscle strength in a daily life may have a desire for such technology. In addition to research on enhancing muscle strength, research is also being conducted on gait assistance. In addition to a physical treatment, a gait assistance provided through a device may be desirable to those with lower body handicaps.

SUMMARY

Some example embodiments relate to a torque setting method.

In some example embodiments, the torque setting method may include measuring a rotation angle of a walking assistance apparatus; measuring a rotation angular velocity of the walking assistance apparatus; calculating a torque setting based on the rotation angle and the rotation angular velocity; and setting a torque for the walking assistance apparatus as the torque setting.

In some example embodiments, the measuring the rotation angle and the measuring the rotation angular velocity are measured by at least one potentiometer.

In some example embodiments, the calculating includes calculating a first value associated with the rotation angle; calculating a second value associated with the rotation angular velocity; and calculating the torque setting based on the first value and the second value.

In some example embodiments, the calculating the first value includes calculating the first value based on a first function, and the calculating the second value includes calculating the second value based on a second function.

In some example embodiments, the first function is a function having a normal distribution and the second function is a sigmoidal function.

In some example embodiments, the rotation angle is an angle by which a foot of a user wearing the walking assistance apparatus is rotated relative to a central axis of the user.

In some example embodiments, the rotation angular velocity is a velocity by which the rotation angle changes over time.

In some example embodiments, the method further includes receiving a trigger signal, wherein the setting sets the torque in response to the trigger signal.

In some example embodiments, and the method further includes generating the trigger signal, when a second leg of the user is in contact with a ground, and the second leg differs from a first leg of the user generating the rotation angle.

In some example embodiments, the generating the trigger signal includes generating the trigger signal by a pressure sensor located on a sole of the second leg.

In some example embodiments, the calculating includes calculating a second torque setting based on a first torque setting, the rotation angle, and the rotation angular velocity, and the setting includes setting the torque for the walking assistance apparatus to the second torque setting.

Some example embodiments relate to a torque setting apparatus.

In some example embodiments, the apparatus includes at least one sensor configured to measure a rotation angle and a rotation angular velocity of a walking assistance apparatus; and a processor configured to, calculate a torque setting of the walking assistance apparatus based on the rotation angle and the rotation angular velocity, and set a torque for the walking assistance apparatus as the torque setting.

In some example embodiments, the processor is configured to, calculate a first value associated with the rotation angle, calculate a second value associated with the rotation angular velocity, and calculate the torque setting based on the first value and the second value.

In some example embodiments, the processor is configured to, calculate the first value based on a first function, and calculate the second value based on a second function.

In some example embodiments, the first function is function having a normal distribution and the second function is a sigmoidal function.

In some example embodiments, the rotation angle is an angle by which a foot of a user wearing the walking assistance apparatus is rotated relative to a central axis of the user.

In some example embodiments, the apparatus further includes a communicator configured to receive a trigger signal, wherein the processor is configured to set the torque in response to the trigger signal.

In some example embodiments, the apparatus further includes a pressure sensor configured to generate the trigger sensor, wherein the generating comprises generating the trigger signal when a second leg of a user is in contact with a ground, and the second leg differs from a first leg of the user generating the rotation angle.

In some example embodiments, the pressure sensor is configured to generate the trigger signal based on a pressure on a sole of the second leg of the user.

In some example embodiments, the processor is configured to, calculate a second torque setting as the torque setting based on a first torque setting, the rotation angle, and the rotation angular velocity, and set the torque for the walking assistance apparatus to the second torque setting.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
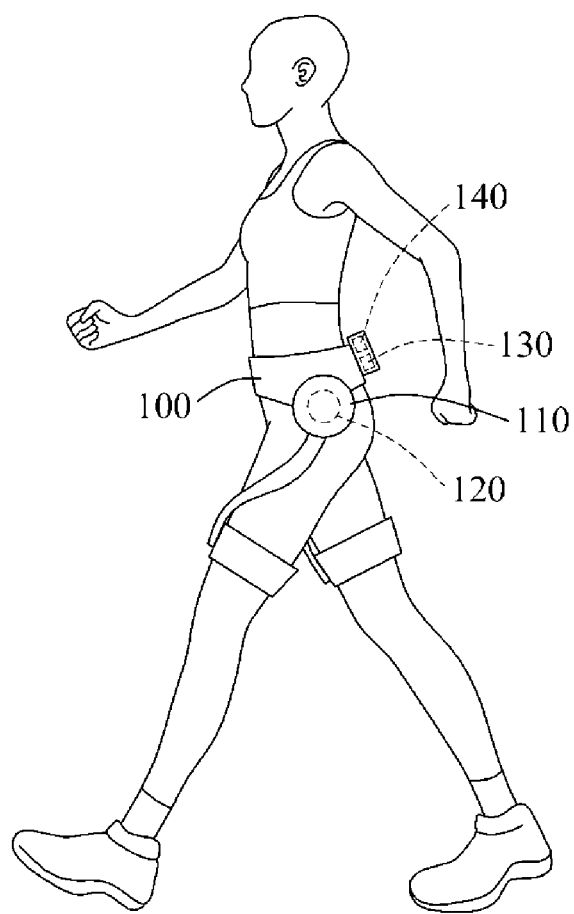
FIG. 1 illustrates an example of a walking assistance apparatus.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which these example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

FIG. 1 illustrates an example of a walking assistance apparatus 100.

Referring to FIG. 1, the walking assistance apparatus 100 may be attached to a user to assist a gait of the user. The walking assistance apparatus 100 may be, for example, a wearable device.

Although FIG. 1 illustrates the walking assistance apparatus 100 provided as, for example, a hip-type walking assistance apparatus, a type of the walking assistance apparatus 100 is not limited thereto. The walking assistance apparatus 100 may be applicable to, for example, a walking assistance apparatus that supports an entire pelvic limb, a walking assistance apparatus that supports a portion of a pelvic limb, and the like. The walking assistance apparatus that supports a portion of a pelvic limb may be applicable to, for example, a walking assistance apparatus that supports up to a knee, and a walking assistance apparatus that supports up to an ankle.

Although, with reference to FIG. 1, the following descriptions are provided based on the hip-type walking assistance apparatus as an example, a type of the walking assistance apparatus is not limited thereto. Thus, this disclosure may be applicable to any apparatus for assisting a gait of a user.

In an example, the walking assistance apparatus 100 may include a driver 110, a sensor 120, an inertial measurement unit (IMU) 130, and a controller 140.

In some example embodiments, the driver 110 may include a pair of drivers 110 that are disposed on respective ones of a left hip portion and a right hip portion of a user to drive the respective ones of hip joints of the user. However, example embodiments are not limited thereto. For example, in other example embodiments, the driver 110 may only be installed on one of the left hip portion and the right hip portion of the user. In some example embodiments, the driver 110 may include a motor (not shown) to generate a rotation torque.

The sensor 120 may measure hip joint angle information of the user while the user is walking. The hip joint angle information may include at least one of angles of both hip joints (or, alternatively, a single hip joint), a difference in the angles of the hip joints, and moving directions of the hip joints. In some example embodiments, the sensor 120 may be included in the driver 110.

In some example embodiments, the sensor 120 may include at least one potentiometer. The potentiometer may be configured to sense at least one of R-axial and L-axial joint angle velocities and R-axial and L-axial joint angles based on a gait motion of the user.

The IMU sensor 130 may measure acceleration information and posture information while the user is walking. For example, the IMU sensor 130 may sense at least one of X-axial, Y-axial, and Z-axial angular velocities and X-axial, Y-axial, and Z-axial accelerations based on the gait motion of the user. The walking assistance apparatus 100 may detect a landing time of a foot of the user based on the acceleration information measured by the IMU sensor 130.

As discussed below with reference to FIG. 11, a pressure sensor (not shown) may be located on a sole of the user to detect the landing time of the foot of the user. Descriptions related to the pressure sensor will be provided with reference to FIG. 11.

The walking assistance apparatus 100 may also include a sensor, for example, an electromyogram (EMG) sensor configured to sense a change in a biosignal or an amount of exercise of the user based on the gait motion of the user as well as the sensor 120 and the IMU sensor 130.

The controller 140 may control the driver 110 to output a torque, for example, an assisting torque, for assisting the user to walk. As an example, a hip-type walking assistance apparatus may include two drivers disposed on, for example, a left hip portion and a right hip portion. The controller 140 may output a control signal to control the driver 110 to generate the torque.

Based on the control signal output from the controller 140, the driver 140 may generate the torque.

The torque may be set by an external source, and may also be set by the controller 140.

Figure 2:
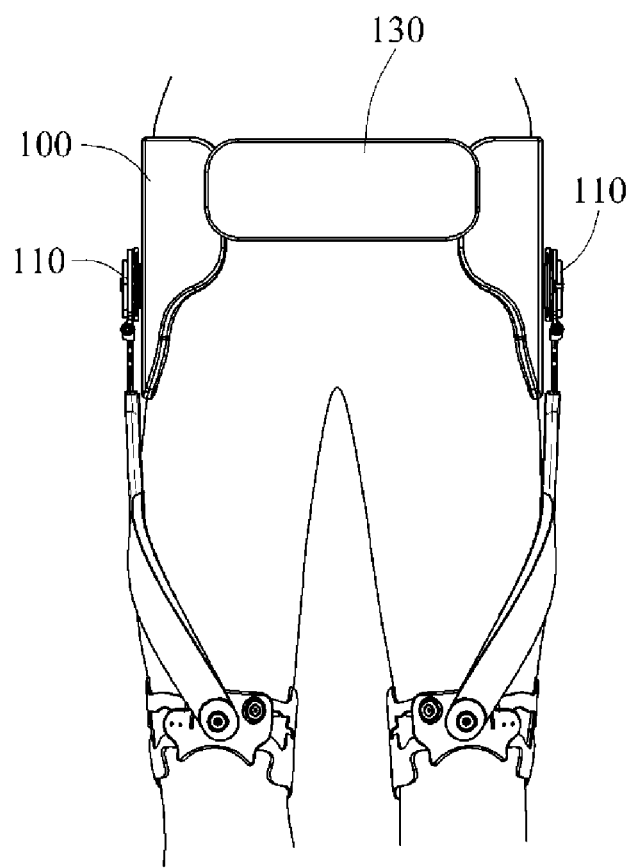
FIG. 2 illustrates another example of a walking assistance apparatus.

FIG. 2 illustrates another example of the walking assistance apparatus 100.

Referring to FIG. 2, the walking assistance apparatus 100 may include the driver 110 provided for a right leg and the driver 110 provided for a left leg.

In some example embodiments, the controller 140 may include a plurality of controllers 140 each associated with controlling a respective one of the drivers 110. However, example embodiments are not limited thereto. For example, in other example embodiments, the controller 140 may be configured to control the drivers 110 on both sides.

Although descriptions are provided that FIG. 2 illustrates a front side of the walking assistance apparatus 100 as an example, FIG. 2 is also be understood as illustrating a rear side of the walking assistance apparatus 100 depending on an example.

In an example, a torque signal may be set for the driver 110 based on an operation state of the walking assistance apparatus 100. The driver 110 may generate a torque based on the set torque signal. For example, the torque signal may be set for the driver 110 based on a gait frequency of the walking assistance apparatus 100.

In another example, the walking assistance apparatus 100 may adjust the torque signal based on an operation result of the walking assistance apparatus 100. For example, the operation result may be provided as a feedback.

As an example, the walking assistance apparatus 100 may calculate the torque signal based on a positive feedback. The walking assistance apparatus 100 may construct a closed loop to calculate the torque signal.

Figure 3:
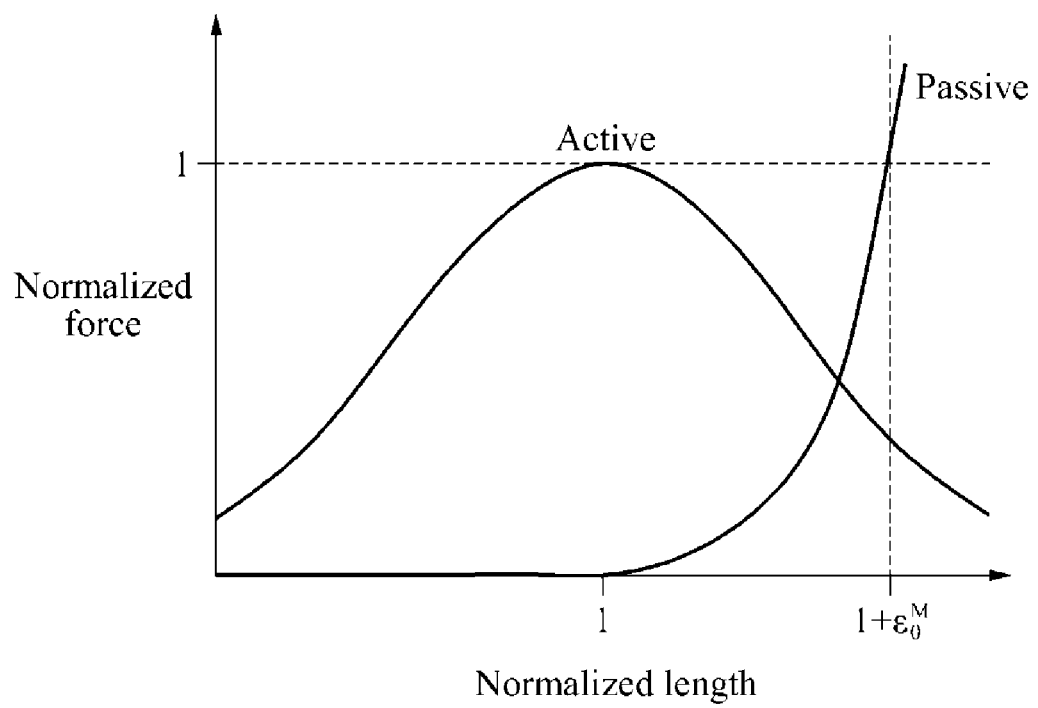
FIG. 3 illustrates an example of a relationship between a length of a muscle and a force to be generated.
Figure 4:
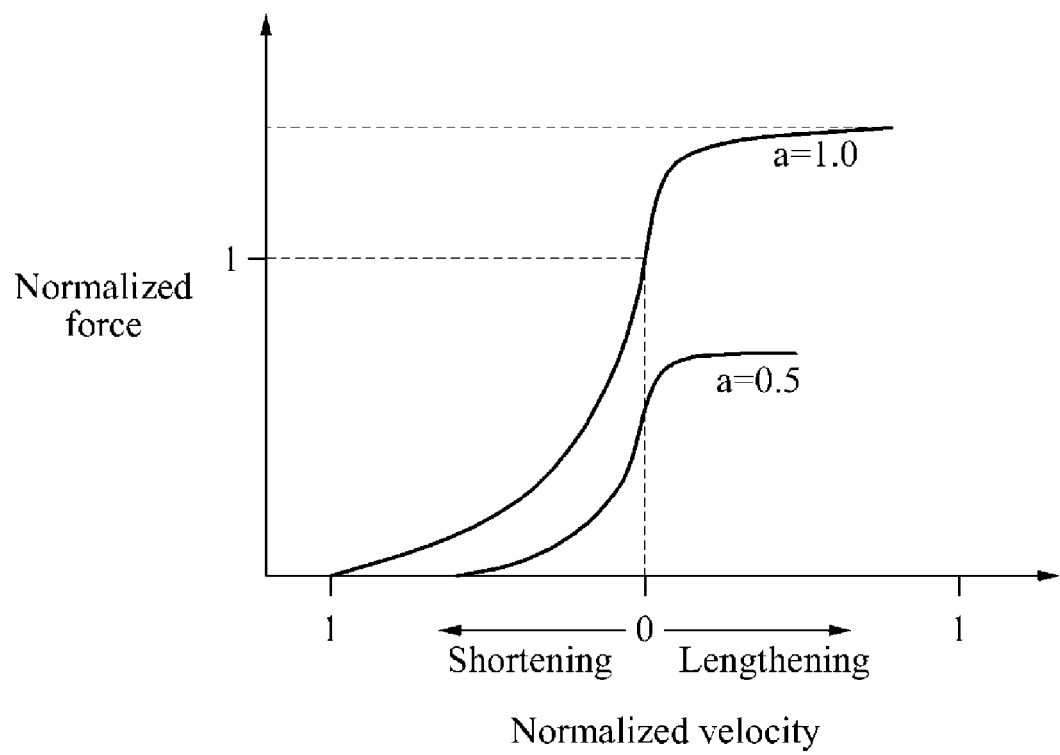
FIG. 4 illustrates an example of a relationship between a flexion speed of a muscle and a force to be generated.

FIGS. 3 and 4 illustrate examples of a biological muscle model.

A hill type muscle model studied in a medical engineering field may have two features.

As one feature, when a stimulation signal is input to a muscle, the input stimulation signal may be amplified proportionally to a force generated by the muscle. Here, the aforementioned phenomenon may also be referred to as, for example, a positive feedback.

As another feature, the force, for example, a muscular force, amplified in response to the stimulation signal may have a desired (or, alternatively, a predetermined) relational formula based on a length of the muscle and a flexion speed of the muscle.

FIG. 3 illustrates an example of a relationship between a length of a muscle and a force to be generated.

A graph of FIG. 3 represents that muscle strength is relatively low when a degree of muscle extension and a degree of muscle flexion are maximized. For example, the graph of FIG. 3 represents that the muscle strength is maximized when a muscle has an appropriate length, for example, in a middle region between where the degree of muscle flexion is minimum and maximum.

FIG. 4 illustrates an example of a relationship between a flexion speed of a muscle and a force to be generated according to at least one example embodiment.

A graph of FIG. 4 represents a force generated based on a velocity of a change in a length of a muscle. As shown in the graph, the generated force increases according to an increase in the velocity.

Figure 5:
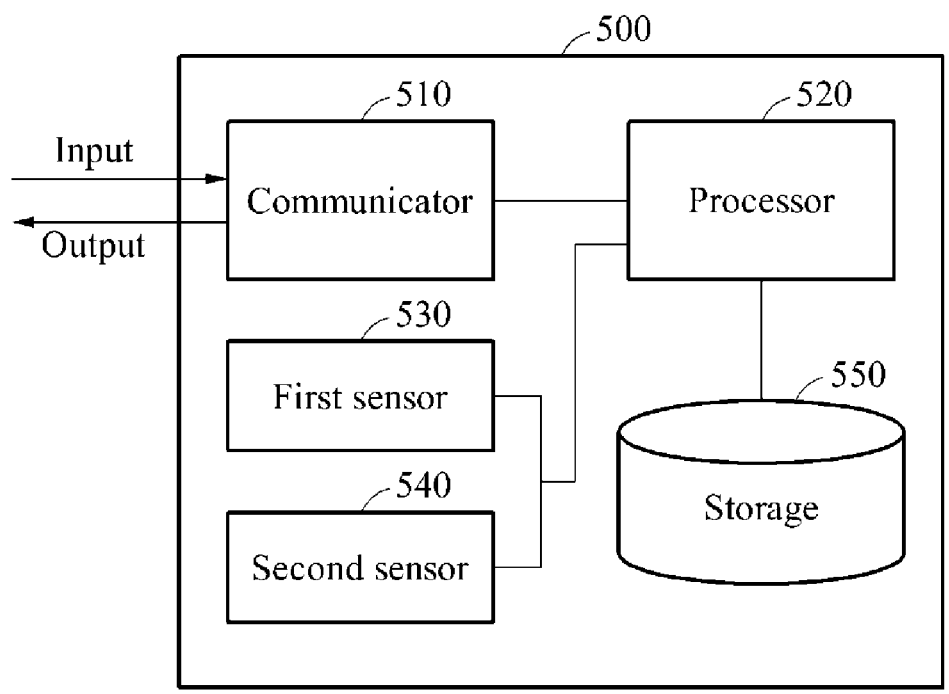
FIG. 5 is a block diagram illustrating an example of a controller of a walking assistance apparatus.

FIG. 5 is a block diagram illustrating an example of a controller 500 of a walking assistance apparatus.

The controller 500 may correspond to the controller 140 of FIG. 1. In some example embodiments, the controller 500 may perform the functions of a torque setting apparatus. For example, the walking assistance apparatus 100 may include the controller 500 as the torque setting apparatus.

Referring to FIG. 5, the controller 500 may include a communicator 510, a processor 520, a first sensor 530, a second sensor 540, and a storage 550.

The communicator 510 may exchange data with other elements of the walking assistance apparatus 100 connected to the controller 500. For example, the processor 520 may transfer a signal to the driver 110 using the communicator 510.

The first sensor 530 may measure a rotation angle of the walking assistance apparatus 100. The rotation angle of the walking assistance apparatus 100 may be, for example, an angle by which the driver is rotated.

The second sensor 540 may measure a rotation angular velocity of the walking assistance apparatus 100. The rotation angular velocity of the walking assistance apparatus 100 may be, for example, an angular velocity at which the driver 110 is rotated.

In some example embodiments, the first sensor 530 and the second sensor 540 may each be discrete sensors provided separately. However, example embodiments are not limited thereto. For example, in another example embodiment, the first sensor 530 and the second sensor 540 may be included in a single sensor, for example, the sensor 120. When the first sensor 530 and the second sensor 540 are included in the single sensor, the descriptions related to the first sensor 530 and the second sensor 540 may be understood as descriptions about the single sensor.

The storage 550 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The storage 550 may store a profile for calculating a torque. For example, the storage 550 may store a function for calculating a first value corresponding to the measured rotation angle and a function for calculating a second value corresponding to the measured rotation angular velocity.

The processor 520 may be implemented by at least one semiconductor chip disposed on a printed circuit board. The processor 520 may be an arithmetic logic unit, a digital signal processor, a microcomputer, a field programmable array, a programmable logic unit, a microprocessor or any other device capable of responding to and executing instructions in a defined manner such that the processor 520 is programmed with instructions that configure the processor into a special purpose computer to perform the operations illustrated in one or more of FIGS. 6-12, such that the processor 520 is configured to instruct the driver 110 to provide a level of torque that is similar to an actual muscle model of a user. For example, the processor 520 may instruct the driver 110 to provide a torque having a rotation angle and rotation angular velocity that is similar to a change in a length and a linear velocity of the actual muscle of the user. Therefore, the processor 520 may improve the functioning of the walking assistance apparatus 100 itself by providing a torque similar to the actual muscular movement of the user.

The processor 520 may process data provided from the communicator 510, the first sensor 530, the second sensor 540, and the storage 550. The processor 520 may generate a signal for generating a torque, for example, a torque signal by processing the provided data.

Descriptions related to the communicator 510, the processor 520, the first sensor 530, the second sensor 540, and the storage 540 will also be provided with reference to FIGS. 6 through 12.

Figure 6:
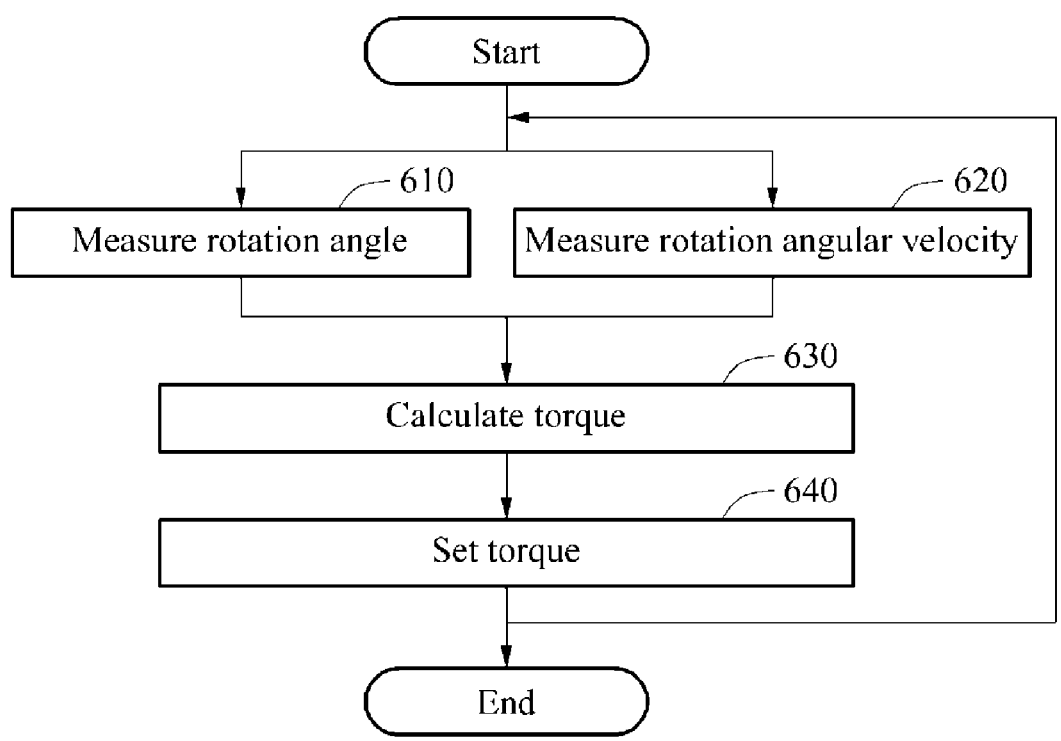
FIG. 6 is a flowchart illustrating an example of a torque setting method.

FIG. 6 is a flowchart illustrating an example of a torque setting method.

Referring to FIG. 6, a torque signal generating method will be described through operations 610 through 640. When a generated torque signal is set for the driver 110, the walking assistance apparatus 100 may perform an operation. Hereinafter, the walking assistance apparatus 100 may also be referred to as, for example, an apparatus 100.

In operation 610, the first sensor 530 may measure a rotation angle of the apparatus 100. For example, the first sensor 530 may measure a rotation angle of the driver 110 in the apparatus 100.

The rotation angle may be, for example, an angle by which a foot of a user wearing the driver 110 is rotated based on a central axis of the user. The central axis of the user may be perpendicular to a surface of a ground.

In some example embodiments, when the controller 500 controls the driver 110 located on a first leg of the user, the first sensor 530 may measure a rotation angle of the driver 110 located on a second leg of the user.

In other example embodiments, when the controller 500 controls the drivers 110 located on both legs of the user, the first sensor 530 may measure rotation angles of both of the drivers 110.

In operation 620, the second sensor 540 may measure a rotation angular velocity of the apparatus 100. For example, the second sensor 540 may measure a rotation angular velocity of the driver 110 in the apparatus 100.

The rotation angular velocity may be, for example, a velocity of the rotation angle changing over time.

In some example embodiments, operations 610 and operation 620 may be performed in parallel (or, alternatively, simultaneously). In other example embodiments, operation 610 may be performed before or after operation 620.

In operation 630, the processor 520 may calculate a torque based on the rotation angle and the rotation angular velocity.

Descriptions related to a torque calculating method will be provided with reference to FIGS. 7 through 9 and 12. As discussed below with reference to FIG. 12, in some example embodiments, the processor 520 may calculate the torque T in accordance with Equation 1, discussed below.

In operation 640, the processor 520 may set the calculated torque for the driver 110. For example, the processor 520 may set a torque signal indicating the calculated torque for the driver 110.

After operation 640 is performed, operation 610 and operation 620 may be performed again.

In an example, in a process of re-performing operation 630, a torque may be calculated based on a torque set in a previous loop. To calculate a current torque, the torque calculated in the previous torque may be applied as a form of a positive feedback.

Figure 12:
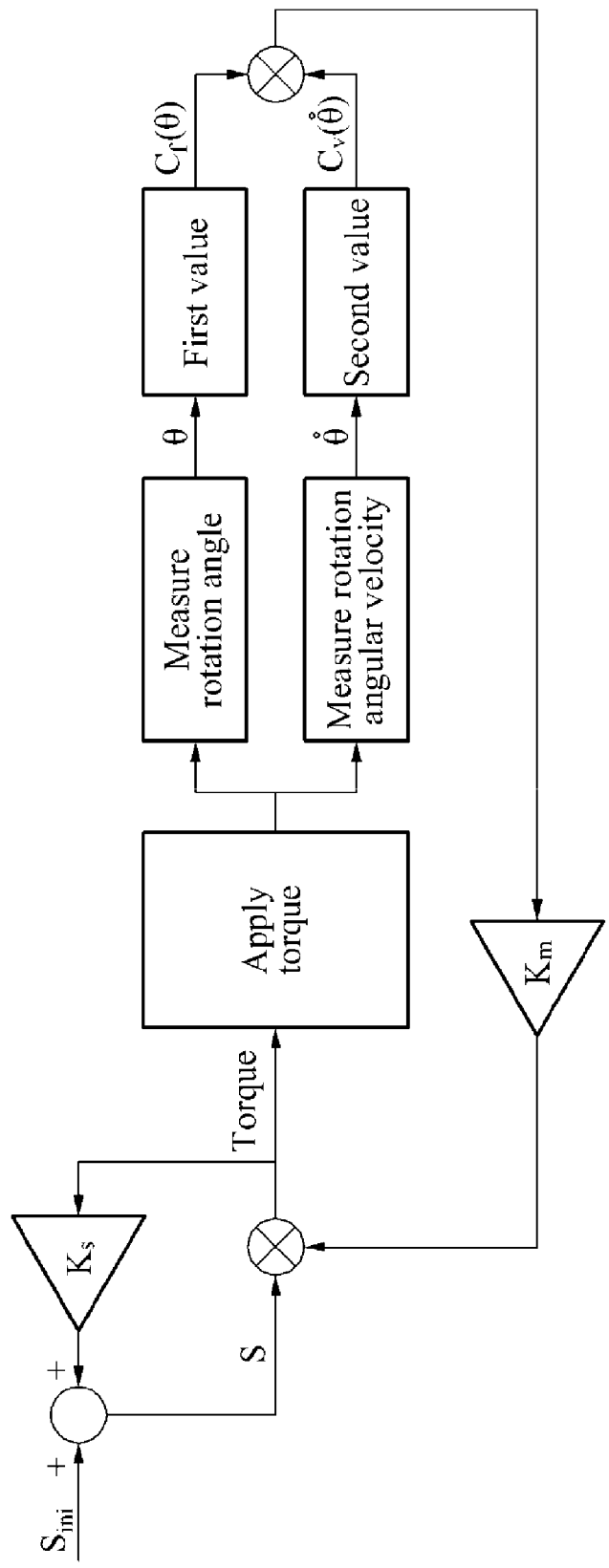
FIG. 12 illustrates an example of a processor calculating a torque in a closed loop.

Descriptions related to a method of calculating a torque based on the positive feedback will be provided with reference to FIG. 12.

Figure 7:
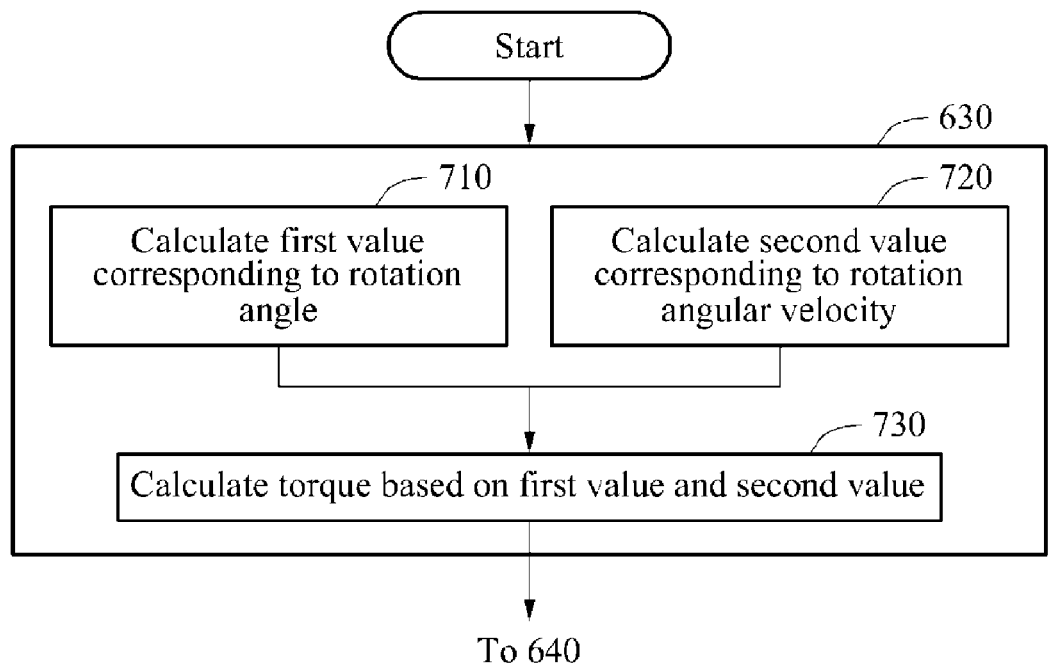
FIG. 7 is a flowchart illustrating an example of a torque calculating method.

FIG. 7 is a flowchart illustrating an example of a torque calculating method.

Operation 630 may include operations 710 through 730.

In operation 710, the processor 520 may calculate a first value corresponding to a rotation angle.

In an example, the processor 520 may calculate the first value corresponding to the rotation angle based on a first function stored in the storage 550. Descriptions related to the first function will be provided as an example with reference to FIG. 8.

In operation 720, the processor 520 may calculate a second value corresponding to a rotation angular velocity.

In an example, the processor 520 may calculate the second value corresponding to the rotation angular velocity based on a second function stored in the storage 550. Descriptions related to the second function will be provided as an example with reference to FIG. 9. In some example embodiments, the processor 520 may perform operation 720 before operation 710.

In operation 730, the processor 520 may calculate a torque based on the first value and the second value.

For example, the processor 520 may calculate the torque based on a value obtained by multiplying the first value and the second value.

Figure 8:
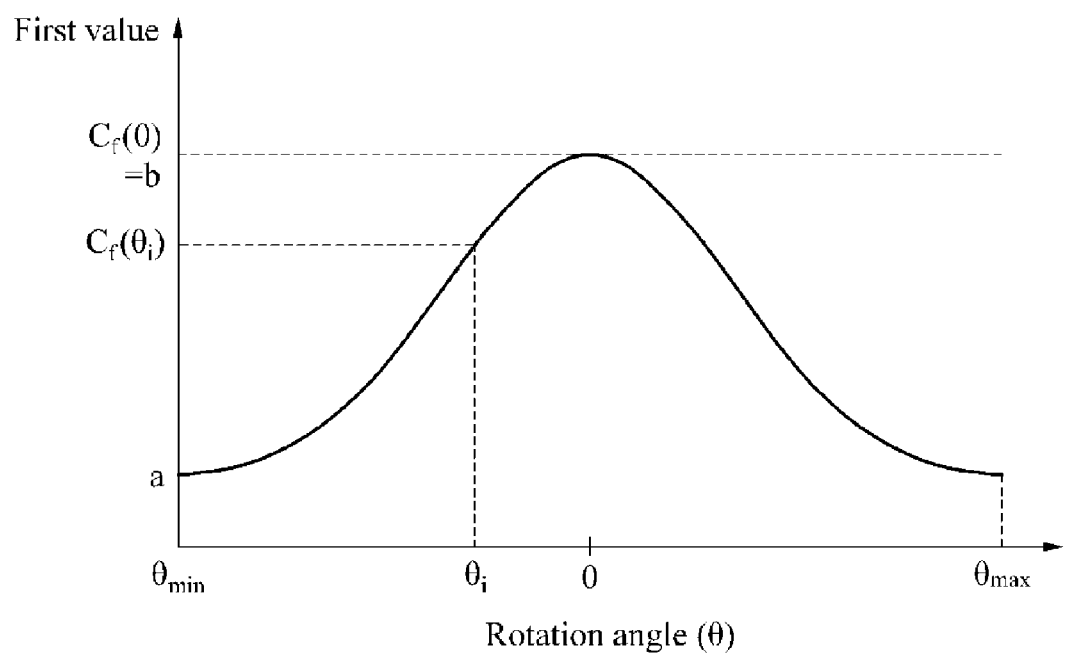
FIG. 8 illustrates an example of a function expressing a first value corresponding to a rotation angle.

FIG. 8 illustrates an example of a function expressing a first value corresponding to a rotation angle according to at least one example embodiment.

Referring to FIG. 8, $\theta$ indicates a rotation angle, and $C_f(\theta)$ indicates a first value.

$\theta_{min}$ indicates a minimum value of the rotation angle, and $\theta_{max}$ indicates a maximum value of the rotation angle.

In an interval in which a value of the rotational angle $\theta$ corresponds to a range between the minimum rotational angle $\theta_{min}$ and a rotational angle of zero (0), a leg including the driver 110 may be located in a rear area relative to an upper body. In an interval in which the value of the rotational angle $\theta$ corresponds to a range between the rotational angle of zero 0 through the maximum rotational angle $\theta_{max}$, the leg including the driver 110 may be located in a front area relative to the upper body. When the value of the rotational angle $\theta$ is 0, the leg may be in a straight line with the upper body.

An interval between $\theta_{min}$ and $\theta_{max}$ may be an interval in which a leg swings for a gait. When the rotation angle changes from $\theta_{min}$ to $\theta_{max}$, a user may be in a state of taking a step with a first leg including the driver 110 to perform the gait. Alternatively, when the rotation angle changes from $\theta_{max}$ to $\theta_{min}$, the first leg may support a body while a second leg is swinging.

The processor 520 may calculate a first value corresponding to the measured rotation angle based on a first function. The first value may be, for example, a value within a range between a minimum (a) and a maximum (b), the range a to b may be a desired (or, alternatively, a predetermined range).

Based on the first function, the maximum value (b) may be obtained as the first value when the rotation angle is 0, and a minimum value (a) may be obtained as the first value when the rotation angle is $\theta_{min}$ and $\theta_{max}$.

In an example, the first function may be in a form of a normal distribution. The aforementioned feature of the first function may indicate a relationship similar to a relationship of a force generated by a muscle based on a length of the muscle in practice.

Figure 9:
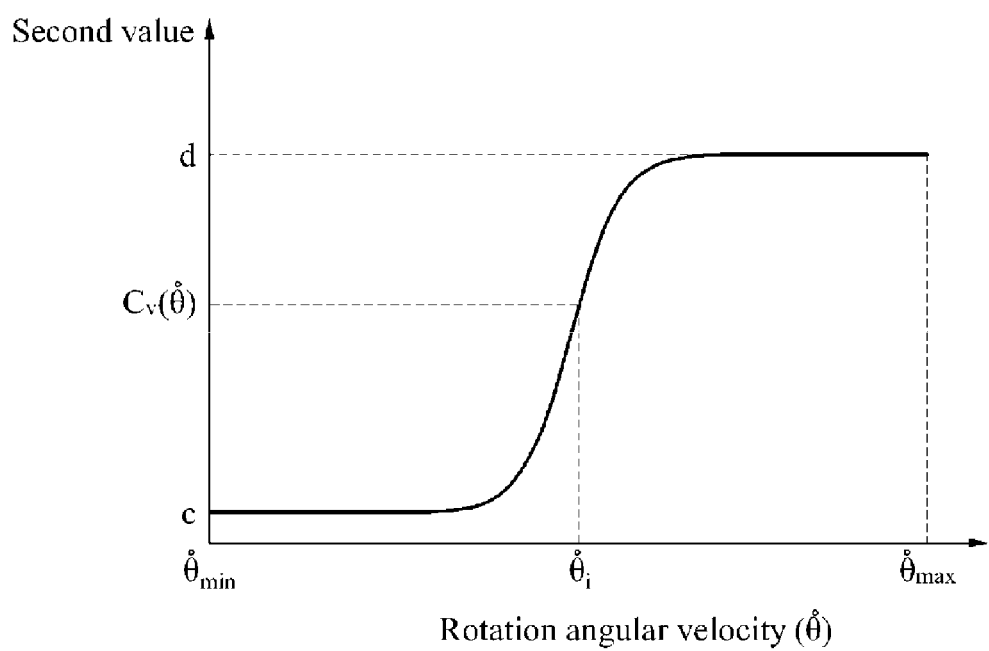
FIG. 9 illustrates an example a function expressing a second value corresponding to a rotation angular velocity.

FIG. 9 illustrates an example a function expressing a second value corresponding to a rotation angular velocity according to at least one example embodiment.

Referring to FIG. 9, $\dot{\theta}$ indicates a rotation angular velocity, and $C_v(\dot{\theta})$ indicates a second value. The second value may be, for example, a value within a range between c and d. The range c to d may be a desired (or, alternatively, a predetermined) range.

$\dot{\theta}_{min}$ indicates a minimum value of the rotation angular velocity, and $\dot{\theta}_{max}$ indicates a maximum value of the rotation angular velocity.

When a value of $C_v(\dot{\theta})$ is large, the rotation angular velocity $\dot{\theta}$ may be relatively high. Also, when the value of $C_v(\dot{\theta})$ is small, the rotation angular velocity $\dot{\theta}$ may be relatively low.

As an example, when a first leg including the driver 110 moves fast, the value of the rotational angular velocity $\dot{\theta}$ may be large. Also, when the first leg moves slowly, the value of the value of the rotational angular velocity $\dot{\theta}$ may be small.

Based on a second function, the second value $C_v(\dot{\theta})$ may increase according to an increase in the value of rotation angular velocity $\dot{\theta}$ until reaching a determined (or, alternatively, a predetermined) interval. From the determined (or, alternatively, the predetermined) interval, the second value $C_v(\dot{\theta})$ may be maintained to be the same. The second function may be in a form of a sigmoid. For example, the second function may be a mathematical function having an "S" shape sigmoid curve. For example, the second function may be a bounded differentiable real function that is defined for all real input values and has a positive derivative at each point.

The aforementioned feature of the second function may indicate a relationship similar to a relationship of a force generated by a muscle based on an extension velocity of the muscle in practice.

By applying the first function and the second function to a torque calculation, a change in a length of an actual muscle and a linear velocity of the actual muscle may be imitated by the rotation angle and the rotation angular velocity of the driver 110 or a motor. Concisely, the driver 110 may be used to express a joint of a user to which a rotating type muscle is attached.

Figure 10:
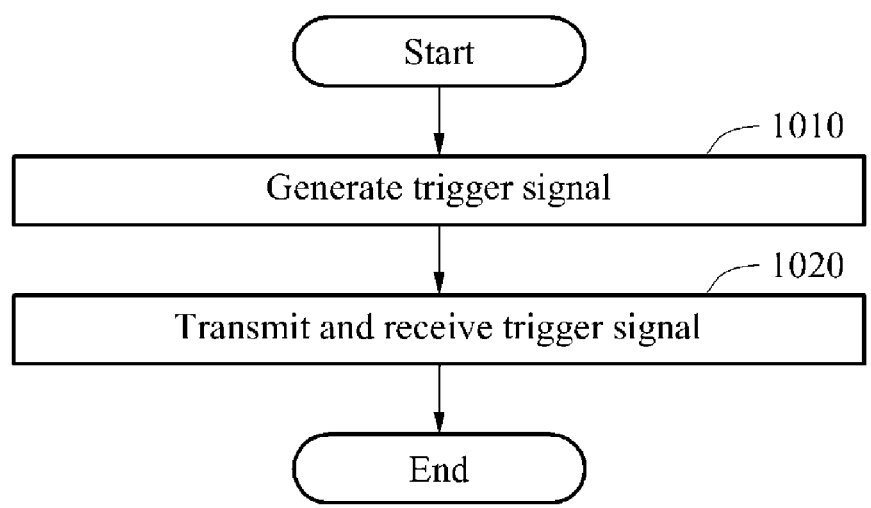
FIG. 10 is a flowchart illustrating an example of generating a trigger signal, and transmitting and receiving the generated trigger signal.

FIG. 10 is a flowchart illustrating an example of generating a trigger signal, and transmitting and receiving the generated trigger signal according to at least one example embodiment.

Referring to FIG. 10, a torque signal may not be set for the driver 110. For example, the driver 110 may provide an assistance torque in response to a swing of a leg. When the leg is supporting a body in lieu of swinging, the driver 110 may not provide the assistance torque based on a rotation angle.

When the leg is supporting the body, the driver 110 may provide a torque set in advance.

In an example, a torque signal to be transmitted to the driver 110 may be generated only when a trigger signal is received.

Operations 1010 and 1020 may be performed in parallel with the foregoing operations 610 through 640.

The controller 500 may further include a pressure sensor. The pressure sensor may be located around a sole of a foot of a user. The pressure sensor may measure a pressure applied to the sole. Descriptions related to a location of the pressure sensor will be provided with reference to FIG. 11.

In operation 1010, the pressure sensor may generate a trigger signal.

In an example, the pressure sensor may generate the trigger signal when the measured pressure exceeds a preset threshold.

The trigger signal may be generated when a second leg of a user is in contact with a ground. Here, the second leg may be a leg differing from a first leg of the user generating a rotation angle. When a swing of a leg moving forward, for example, the first leg ends, the trigger signal may be generated for a swing of a leg supporting a body, for example, the second leg.

In operation 1020, the pressure sensor may transmit the trigger signal to the communicator 510. The communicator 510 may receive the trigger signal from the pressure sensor.

In an example, the pressure sensor may wired or wirelessly transmit the trigger signal to the communicator 510, and the communicator 510 may wired or wirelessly receive the trigger signal from the pressure sensor. The pressure sensor and the communicator 510 may use, for example, Bluetooth for a wireless communication.

In response to the received trigger signal, the processor 520 may perform operation 640. Therefore, in operation 640, the processor 520 may further determine whether the trigger signal is received.

In operation 640, the processor 520 may set a torque signal for the driver 110 in response to the received trigger signal.

Figure 11:
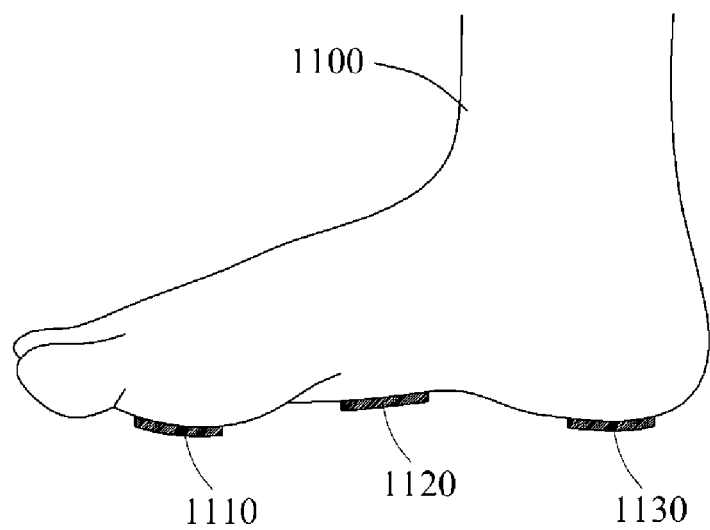
FIG. 11 illustrates an example of a pressure sensor.

FIG. 11 illustrates an example of a pressure sensor.

The pressure sensor may be located around a sole of a foot 1100 of a user. As an example, the pressure sensor may be disposed under the sole. As another example, the pressure sensor may be attached to a shoe of the user to measure a pressure applied to the sole.

In an example, a plurality of pressure sensors may be provided. A plurality of pressure sensors 1110 through 1130 may measure pressures applied to portions of the sole. As an example, a trigger signal may be generated when a pressure measured by the pressure sensor 1130 disposed on a heel of the foot exceeds a threshold.

FIG. 12 illustrates an example of a processor calculating a torque in a closed loop.

Referring to FIGS. 6 and 12, a closed loop may form a positive feedback.

In operation 640, the processor 520 may calculate the torque T based on Equation 1.

$$T = K_m C_f(\theta) C_v(\dot{\theta}) S \quad \text{[Equation 1]}$$

In Equation 1, T denotes the torque, $K_m$ denotes gain set for a system, $C_f(\theta)$ denotes a first value, $C_v(\dot{\theta})$ denotes a second value, and S denotes a having signal.

The processor 520 may calculate the having signal S based on Equation 2.

$$S = S_{ini} + K_s T \quad \text{[Equation 2]}$$

In Equation 2, $S_{ini}$ denotes an initial having signal, and $K_s$ denotes preset gain. $K_s$ may be adjusted based on a system.

The initial having signal $S_{ini}$ may be input in response to the received trigger signal.

The processor 520 may calculate the torque T based on the positive feedback such that the driver operates similarly or identically to an actual muscle. A user wearability may be improved based on a method of calculating a torque based on a positive feedback.

In the foregoing operation 630, the processor 520 may calculate a second torque based on a first torque set for an apparatus, a rotation angle, and a rotation angular velocity.

The first torque may be, for example, a torque calculated through a previous loop to be set for the driver 110. The second torque may be, for example, a current torque to be set.

In operation 640, the processor 520 may set a torque signal of the second torque to the driver 110.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A torque setting method comprising:
measuring a rotation angle of a walking assistance apparatus;
measuring a rotation angular velocity of the walking assistance apparatus;
calculating a torque setting by applying the rotation angle to a first function having a normal distribution and the rotation angular velocity to a second function having a sigmoidal distribution; and
setting a torque for the walking assistance apparatus as the torque setting.

2. The method of claim 1, wherein the measuring the rotation angle and the measuring the rotation angular velocity are measured by at least one potentiometer.

3. The method of claim 1, wherein the calculating comprises:
calculating a first value associated with the rotation angle;
calculating a second value associated with the rotation angular velocity; and
calculating the torque setting based on the first value and the second value.

4. The method of claim 3, wherein
the calculating the first value comprises calculating the first value based on the first function, and
the calculating the second value comprises calculating the second value based on the second function.

5. The method of claim 4, wherein the first function is a function having the normal distribution and the second function is a sigmoidal function.

6. The method of claim 1, wherein the rotation angle is an angle by which a foot of a user wearing the walking assistance apparatus is rotated relative to a central axis of the user.

7. The method of claim 1, wherein the rotation angular velocity is a velocity by which the rotation angle changes over time.

8. The method of claim 1, further comprising:
receiving a trigger signal, wherein
the setting sets the torque in response to the trigger signal.

9. The method of claim 8, further comprising:
generating the trigger signal,
wherein the generating comprises generating the trigger signal when a second leg of the user is in contact with a ground, and the second leg differs from a first leg of the user generating the rotation angle.

10. The method of claim 9, wherein the generating the trigger signal comprises:
generating the trigger signal by a pressure sensor located on a sole of the second leg.

11. The method of claim 1, wherein
the calculating comprises calculating the torque setting associated with a current iteration based on the torque setting associated with a prior iteration, the rotation angle, and the rotation angular velocity, and
the setting comprises setting the torque for the walking assistance apparatus to the torque setting associated with the current iteration.

12. A torque setting apparatus comprises:
at least one sensor configured to measure a rotation angle and a rotation angular velocity of a walking assistance apparatus; and
a processor configured to,
calculate a torque setting of the walking assistance apparatus by applying the rotation angle to a first function having a normal distribution and the rotation angular velocity to a second function having a sigmoidal distribution, and
set a torque for the walking assistance apparatus as the torque setting.

13. The apparatus of claim 12, wherein the processor is configured to,
calculate a first value associated with the rotation angle,
calculate a second value associated with the rotation angular velocity, and
calculate the torque setting based on the first value and the second value.

14. The apparatus of claim 13, wherein the processor is configured to,
calculate the first value based on the first function, and
calculate the second value based on the second function.

15. The apparatus of claim 14, wherein the first function is function having the normal distribution and the second function is a sigmoidal function.

16. The apparatus of claim 12, wherein the rotation angle is an angle by which a foot of a user wearing the walking assistance apparatus is rotated relative to a central axis of the user.

17. The apparatus of claim 12, further comprising:
a communicator configured to receive a trigger signal, wherein
the processor is configured to set the torque in response to the trigger signal.

18. The apparatus of claim 17, further comprising:
a pressure sensor configured to generate the trigger signal, wherein the generating comprises generating the trigger signal when a second leg of a user is in contact with a ground, and the second leg differs from a first leg of the user generating the rotation angle.

19. The apparatus of claim 18, wherein the pressure sensor is configured to generate the trigger signal based on a pressure on a sole of the second leg of the user.

20. The apparatus of claim 12, wherein the processor is configured to,
calculate the torque setting as the torque setting associated with a current iteration based on the torque setting associated with a prior iteration, the rotation angle, and the rotation angular velocity, and
set the torque for the walking assistance apparatus to the torque setting associated with the current iteration.

* * * * *